United States Patent [19]

Orejola

[11] 4,388,759
[45] Jun. 21, 1983

[54] ELECTROCARDIOGRAM CALIPER

[76] Inventor: Wilmo C. Orejola, 1630 Phippine Heart Center for Asia, Quezon City, Metro Manila, Philippines

[21] Appl. No.: 295,603

[22] Filed: Aug. 24, 1981

[30] Foreign Application Priority Data

Oct. 15, 1980 [PH] Philippines ............................ UM-4323

[51] Int. Cl.$^3$ ................................................ G01B 5/02
[52] U.S. Cl. .................................... 33/1 C; 33/148 E; 33/149 R
[58] Field of Search .......... 33/1 C, 1 R, 1 HH, 1 SD, 33/148 E, 148 R, 148 F, 149 R, 153 R, 153 E; 235/61 R, 61 E

[56] References Cited

U.S. PATENT DOCUMENTS

| | | | |
|---|---|---|---|
| 1,299,978 | 4/1919 | MacDowney | 33/148 E X |
| 1,317,879 | 10/1919 | Kramer | 33/148 E |
| 2,501,550 | 3/1950 | Tamagna et al. | 33/1 C |
| 3,126,639 | 3/1964 | Larson et al. | 33/1 C X |
| 3,733,708 | 5/1973 | Goodman | 33/148 E |

Primary Examiner—William D. Martin, Jr.
Attorney, Agent, or Firm—Linval B. Castle

[57] ABSTRACT

A caliper calibrated for the direct reading of electrocardiogram tracings. Each arm of the caliper is calibrated and is read by indexing the calibration against a curved index line on the opposite arm which is varied by the spacing between the caliper points. One such calibration represents the duration in seconds of the various deflections or complexes and a second calibration represents the amplitudes of a deflection in millivolts. On the reverse side of the caliper, an arm is calibrated to indicate frequency in deflections per minute between adjacent similar deflections or a count between three such intervals. A pair of coaxial calibrated discs attached for rotation about the caliper pivot provides a rapid and accurate means for the determination of mean vector and therefore axis deviation.

2 Claims, 3 Drawing Figures

ELECTROCARDIOGRAM CALIPER

SUMMARY OF THE INVENTION

This invention relates generally to medical laboratory equipment and particularly to calibrated calipers for the direct and precise reading of electrocardiogram tracings.

Presently available for the reading and interpreting of electrocardiogram tracings in standard ECG paper are various calipers and scales that are used by placing them over the tracings for comparison and counting, a system that is subject to varied interpretations and inaccuracies, while being time-consuming. In determining the rates and intervals from the various deflections on the ECG paper, readers find it most difficult and often inaccurate to count the boxes or squares on the recording tape and to translate them into seconds or millivolts as appropriate. In determining mean vectors or axis deviations of the electrical axis of the heart, the plotting of precise angles and locating positivity or negativity of the limb leads requires keen vision and concentration, which factors may not always be present.

The present invention is for an improved ECG caliper that facilitates the direct and precise readings of deflection amplitudes, rates, intervals and vectors from standard ECG paper tracings. The caliper is easy to produce and is very easy to use and manipulate to obtain direct interpretations from the tracings.

Briefly described, one portion of the ECG caliper comprises a pair of blade-shaped arms pivoted together at a fulcrum at one end and pointed at the other end. The arms are calibrated with rates, frequencies, and amplitudes, the values of which are determined by their intersection with a curved reference line inscribed on the opposite arm. The second portion of the caliper comprises a pair of coaxial discs with overlying indicator attached to and rotatable on the fulcrum. The discs are calibrated with various lead and polarity indications that aid in the determination of mean vector or axis deviation.

DESCRIPTION OF THE DRAWINGS

In the drawings which illustrate the preferred embodiment of the invention.

DETAILED DESCRIPTION

Figure 1:
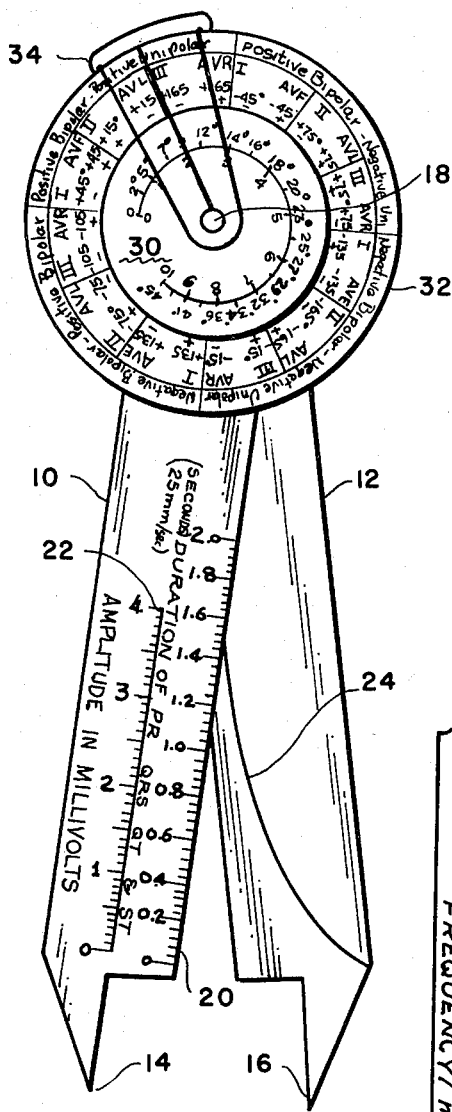
FIG. 1 is a front elevation view of the ECG caliper.
Figure 3:
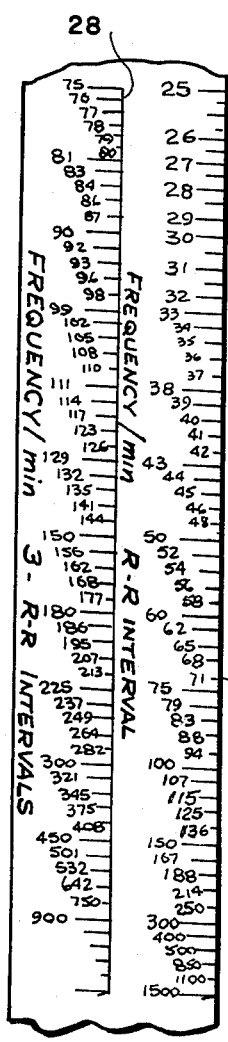
FIG. 3 is an elevation view illustrating the details of the calibration on the caliper blade illustrated in FIG. 2.

FIG. 1 is a front elevation view of the ECG caliper and illustrates two relatively thin but wide blade-shaped arms 10 and 12 having pointed tips 14 and 16, respectively, at one end and connected for planar rotation about a pivot pin 18 adjacent the opposite end.

As illustrated in FIG. 1, the frontal surface of the arm 10 is calibrated with linear calibrations 20 representing duration, in seconds, of tracing deflections of PR, QRS, QT, and ST deflections recorded on ECG tape at a tape velocity of 25 millimeters per second. A second linear scale 22 printed on the frontal surface of the arm 10 indicates deflection amplitudes in millivolts. Both of the scales 20 and 22 are read at the point that a curved line 24 on the surface of the opposite arm 12 intersects the edge of the scale 20. Thus, in the illustrated embodiment, if the pointed tips 14 and 16 were spaced along an ECG tracing between the onset and end of a deflection complex or segment, the intersection of the curved line 24 on the edge of the scale 20 would indicate a duration of 1.5 seconds. If the caliper were used to measure amplitude of a deflection, pointed tips 14 and 16 would be adjusted to measure between the base of the tracing and the peak of the deflection and the scale 22 would then provide an indication of an amplitude of 3.75 millivolts.

Figure 2:
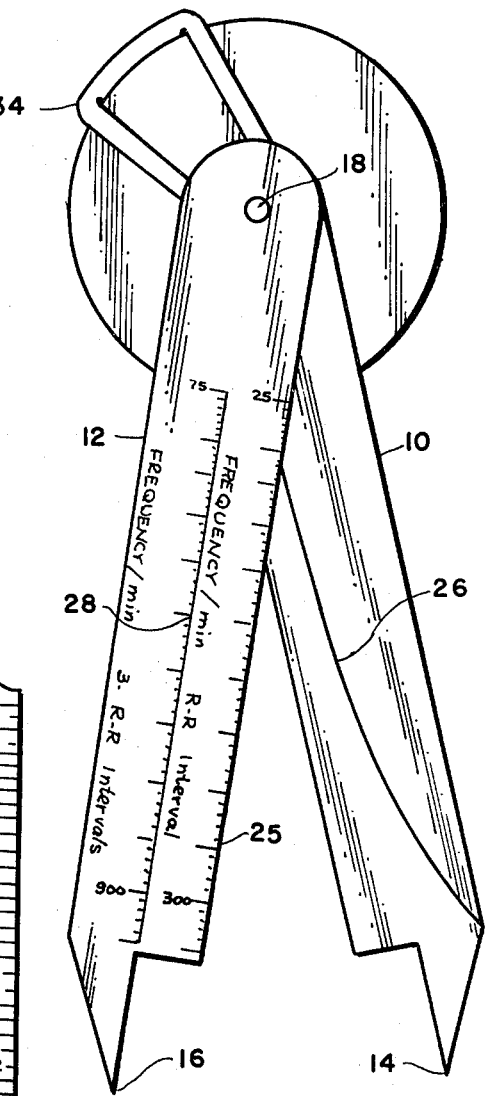
FIG. 2 is a rear elevation view of the ECG caliper.

FIG. 2 is an elevation view of the rear of the calipers, and illustrates the surface of the arm 12 calibrated with a non-linear scale 25 representing the frequency per minute of R deflections occurring in an ECG tracing. To determine such a deflection frequency, the caliper points 14 and 16 are set on the peaks of two successive R, P, or other prominent, deflections and the frequency is read at the intersection of the edge of the scale 25 with a curved line 26 inscribed on the other arm 10 of the caliper. A second scale 28 is also inscribed on the arm 12 adjacent the scale 25. In the scale 28, the calibrations of scale 25 are magnified three-fold in order to more accurately read the tracings at high frequency rates. Therefore, instead of measuring one interval between successive R or P deflections, three intervals between such deflections are indicated with the average being available from a reading of the single interval scale 25.

In determining axis deviation or mean vector from ECG tracings, a smaller diameter vector disc 30, which is coaxial with and overlies the larger diameter disc 32 of FIG. 1 is employed. As illustrated in FIG. 1, smaller diameter disc 30 and larger diameter disc 32 are axially connected to the pivot pin 18. Each of the discs 30 and 32 and also the indicator 34 are freely rotatable about the pivot 18.

As shown in FIG. 1, the disc 32 is divided into four quadrants and indicated in the periphery of each quadrant is the orientation of corresponding perpendicular limb leads; that is, whether the bipolar leads I, II, and III are positive (upright) or negative (inverted) or their perpendicular limb leads, AVF, AVL, and AVR, respectively, are positive or negative, according to the hexaxial system of mean vector determination. Thus, lead I is the perpendicular lead of unipolar lead AVF, lead II of AVL, and lead III of AVR. The inner portion of each of the quadrants in the disc 32 contains the calculated number of degrees in every pair of the perpendicular leads in every form of orientation. It will be noted that underlying each of the indicated calculated degrees in each third quadrant are signs indicating + or −. This indicates that the indicated number of degrees are not fixed and must be adjusted according to a calibration on the vector disc 30.

The vector disc 30 is coaxial with the disc 32 and may be readily rotated. Two rows of numbers are indicated around the periphery of the disc 30. An arc of approximately 300° is divided into ten equal arcuate segments with each segment representing $4\frac{1}{2}°$ of arc so that the total ten-segment arc is calibrated from zero to 45°. The inner numbers are used for translating differences in amplitude between each pair of perpendicular leads. When placed along the lead with greater amplitude, the assigned number of degrees is either added to, or subtracted from the number of degrees assigned in that particular lead in the larger disc 32. The resulting subtraction or addition is then the mean vector or axis deviation determined for that particular ECG tracing.

The indicator 34 which is easily rotated about the pivot 18 aids with the alignment of the figures involved in the determination and provides an accurate and convenient temporary "scratch pad" memory for the ECG technician.

I claim:

1. A caliper for aiding in the rapid determination of deflection amplitudes, intervals and frequencies from standard electrocardiogram tracings, said caliper comprising:

first and second caliper arms, each arm pointed at its first end and coupled together for rotation about a pivot pin at the second end, each of said arms having a wide, blade-shaped construction;

a first calibration on the first surface of said first arm, said first calibration being a linear representation of seconds of duration of a tracing deflection;

a second calibration on the first surface of said first arm, said second calibration being a linear representation of millivolt amplitude of a tracing deflection;

a first curved index line on the second surface of said second arm, said first and second calibrations being read at the intersection of the inner edge of said first arm and said first curved index line;

a third calibration on the first surface of said second arm, said third calibration representing frequency as measured between successive similar deflections and between three such similar deflections; and a second curved index line on the second surface of said first arm, said third calibration being read at the intersection of the inner edge of said second arm and said second curved index line.

2. The caliper claimed in claim 1 further including first and second discs coaxially attached to said pivot pin for rotation thereon;

a first calibration around the periphery of said first disc, said calibration indicating combinations of bipolar leads, perpendicular limb leads, the respective signs according to the hexaxial system and the calculated number of degrees in every pair of perpendicular leads in every form of orientation;

a second calibration around an arc of substantially 300° on said second disc, said calibration representing angles by which said first calibration may be corrected to obtain a determination of mean vector;

said second disc having a smaller diameter than the diameter of said first disc whereby both first and second disc calibrations may be simultaneously observed.

* * * * *